(12) United States Patent
Rohde et al.

(10) Patent No.: US 8,932,242 B2
(45) Date of Patent: Jan. 13, 2015

(54) METHODS AND DEVICES FOR ASSISTING BIRTH

(71) Applicant: BirthBuddies Inc., Novato, CA (US)

(72) Inventors: Sonja C. Rohde, Novato, CA (US); James V. Rohde, Novato, CA (US)

(73) Assignee: BirthBuddies, Inc., Novato, CA (US)

( * ) Notice: Subject to any disclaimer, the term of this patent is extended or adjusted under 35 U.S.C. 154(b) by 0 days.

(21) Appl. No.: 13/870,966

(22) Filed: Apr. 25, 2013

(65) Prior Publication Data

US 2014/0121671 A1    May 1, 2014

Related U.S. Application Data

(63) Continuation of application No. 12/838,259, filed on Jul. 16, 2010, now Pat. No. 8,449,481.

(60) Provisional application No. 61/226,493, filed on Jul. 17, 2009.

(51) Int. Cl.
*A61H 19/00* (2006.01)

(52) U.S. Cl.
USPC ............................................. 601/45; 128/845

(58) Field of Classification Search
USPC .............. 601/45; 482/53, 62, 63, 93, 94, 109, 482/111, 112, 121, 122, 124, 125, 126, 482/907; 128/845
See application file for complete search history.

(56) References Cited

U.S. PATENT DOCUMENTS

| | | | |
|---|---|---|---|
| 324,498 A | 8/1885 | Surbaugh | |
| 459,027 A | 9/1891 | Thompson | |
| 899,434 A | 9/1908 | Reed | |
| 905,301 A | 12/1908 | English | |
| 915,127 A | 3/1909 | Topping | |
| 964,309 A | 7/1910 | Parrott | |
| 1,012,802 A | 12/1911 | Brogan | |
| 2,009,655 A | 7/1935 | Freymann | |
| 3,068,002 A | 12/1962 | Balne | |
| 4,251,071 A | 2/1981 | Norton | |
| 4,909,505 A | 3/1990 | Tee | |
| 5,328,433 A * | 7/1994 | Berman | 482/122 |
| 5,518,486 A | 5/1996 | Sheeler | |
| 7,318,810 B1 * | 1/2008 | Benson | 601/45 |
| 7,481,747 B2 * | 1/2009 | Lechleiter | 482/57 |
| D630,332 S | 1/2011 | Richards | |
| 2001/0008957 A1 | 7/2001 | Rhee | |
| 2004/0053756 A1 | 3/2004 | Tremayne | |
| 2004/0111784 A1 | 6/2004 | Henricksen | |
| 2005/0192169 A1 | 9/2005 | Girgen et al. | |
| 2005/0204455 A1 | 9/2005 | Pelligra | |
| 2008/0045870 A1 | 2/2008 | Nozik et al. | |

OTHER PUBLICATIONS

International Search Report, mailed on Feb. 25, 2011 for International Patent Application No. PCT/US2010/042358, 6 pages.
Written Opinion of the International Searching Authority mailed on Feb. 25, 2011 for PCT Patent Application No. PCT/US2010/042358, 6 pages.
Extended European Search Report mailed Oct. 9, 2014, from European Application No. 10800644.6 (6 pages).

* cited by examiner

*Primary Examiner* — Michael A. Brown
(74) *Attorney, Agent, or Firm* — Kilpatrick Townsend & Stockton LLP

(57) ABSTRACT

Devices and methods for assisting birth are disclosed. The device is constructed from an elastic material with an elongated center and handles at both ends. A patient grasps the device at one end, while the other end is secured. When the patient experiences a contraction, the patient pulls on the device at a downward angle. The device elastically stretches and causes the patient to utilize correct abdominal muscles for pushing a fetus down a birth canal, thus reducing second stage of labor.

11 Claims, 10 Drawing Sheets

FIG. 1E   SECTION A-A

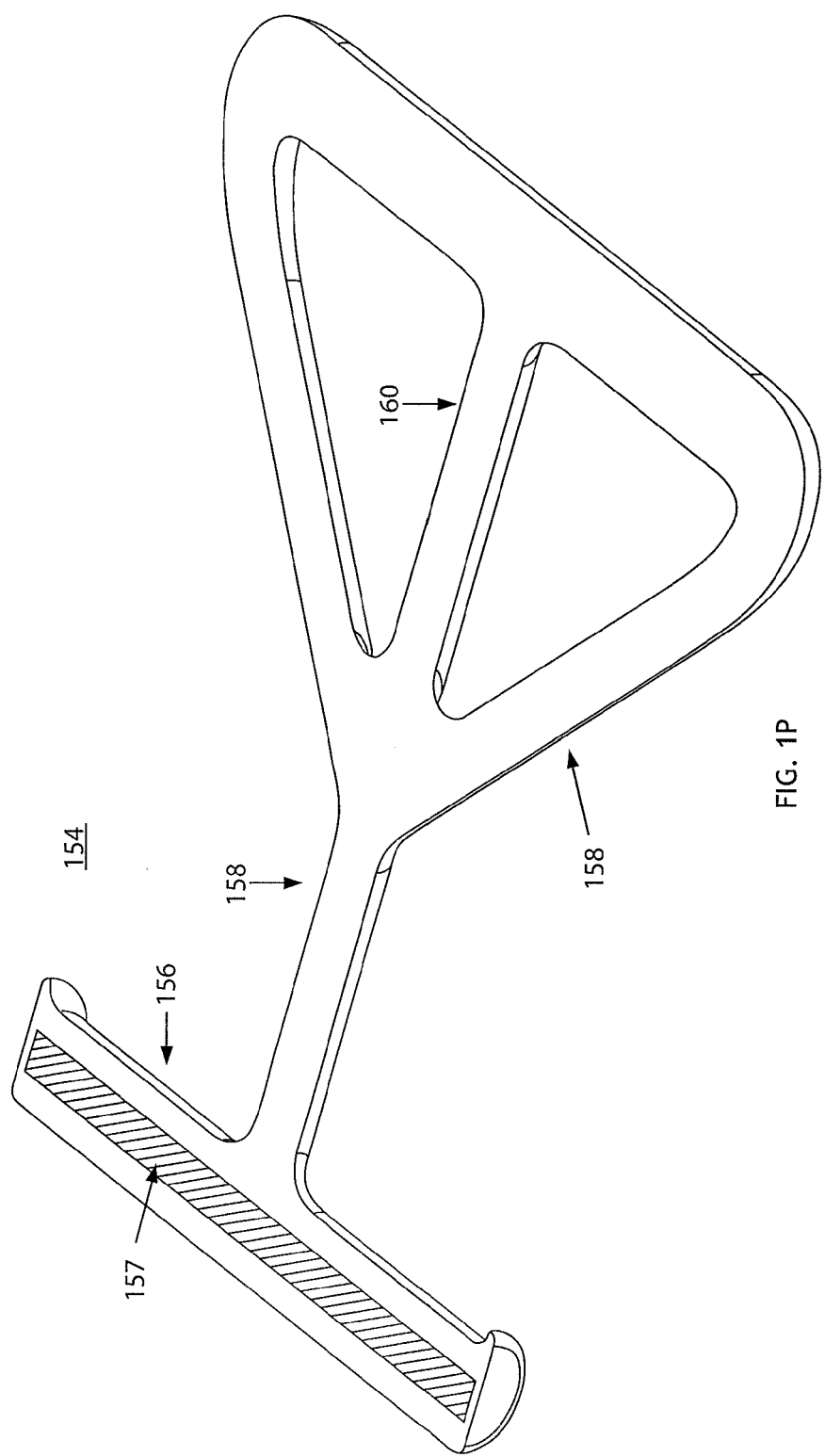

METHODS AND DEVICES FOR ASSISTING BIRTH

CROSS-REFERENCES TO RELATED APPLICATIONS

This application is a continuation of U.S. patent application Ser. No. 12/838,259, filed Jul. 16, 2010, which claims the benefit of U.S. Provisional Application No. 61/226,493, filed on Jul. 17, 2009, the entireties of which are herein incorporated by reference.

BACKGROUND OF THE INVENTION

Embodiments of the invention disclose methods and devices for assisting birth, and more specifically, methods and devices for assisting a patient to utilize correct abdominal muscles during the second stage of labor.

The birthing process includes three stages. The first stage begins with contractions which cause progressive changes in a patient's cervix, and ends when the patient's cervix is fully dilated. The second stage of labor, also known as the pushing stage, takes place between full dilation of the cervix, and the birth of the patient's fetus. The third stage is completed when the placenta exits the patient. During the second stage of labor, proper use of abdominal muscles to contract the uterus is critical for pushing the fetus down the patient's birth canal. If the patient cannot effectively push the fetus out of her birth canal, then an unplanned cesarean section or vacuum extraction may need to be performed.

Devices have been proposed which assist the expectant mother with using her abdominal muscles during the second stage of labor. Use of these devices, however, often requires the patient to have full control of her legs, which can be impossible with the use of epidural anesthesia. Also, these devices may not provide an efficient position for utilizing correct abdominal muscles to push a fetus down a birth canal. Because of these and other disadvantages, the use of (and benefits from) abdominal muscle assist devices for the second stage of labor has been limited.

Accordingly, it would be desirable to provide methods and devices that place a patient in an optimal body position for giving birth, and also require the patient to utilize the correct abdominal muscles for pushing a fetus down a birth canal.

BRIEF SUMMARY OF THE INVENTION

In one embodiment of the invention, a method for assisting birth is disclosed. A pregnant patient in a second stage of labor is positioned in a semi-fowlers or high fowlers position. A first end of an elastic birthing device is secured while a second end is grasp by the patient, with the patient's arms being fully extended or slightly bent. The birthing device is placed so that the first end extends at a downward angle between the patient's legs from the second end. The elastic birthing device is pulled by the patient along the downward direction and elastically stretched between the ends by the patient during a contraction so that the pulling of the elastic birthing device assists in the second stage of labor.

In one aspect of the method, the elastic birthing device may stretch 0.5-2 inches when pulled by the patient with a force ranging from 20-150 lbs.

In another aspect of the method, the downward direction includes a direction at an angle between a horizontal and vertical axis.

In another aspect of the method, securing the first end may include attaching the first end of the elastic birthing device to a bed upon which the patient is positioned.

In another aspect of the method, securing the first end may include manually holding the first end with both hands of another person so that the elastic birthing device is elastically stretched between the patient and the other person.

In another aspect of the method, the elastic birthing device may be manually pulled, by the other person, along the downward angle away from the hands of the patient.

In another aspect of the method, tension on the birthing device may be released when the contraction ceases.

In another aspect of the method, feet of the patient may be positioned on a squatting bar or stirrups.

In another aspect of the method, the elastic birthing device may maintain the patient in the semi-fowlers, high fowlers position or any other position that allows the patients legs to be spread and bent in squatting position when not pulling.

In another aspect of the method, the elastic birthing device may be in tension at the downward angle before pulling, and the elastic birthing device may not noticeably stretch under this tension.

In another embodiment of the invention, a device for assisting a woman to give birth is disclosed. The device includes an elongated center portion with a first end and a second end defining a central axis. A first handle connected to the first end, the first handle configured for gripping with two hands. A second handle connected to the second end, the second handle including at least one loop. The elongated center portion, first handle, and second handle comprise an elastic material.

In one aspect of the device, the elongated center portion may include a cylindrical body with a circular cross-section.

In another aspect of the device, the elongated center portion may include sufficient axial elasticity to increase significantly in length when the woman applies a birth-assisting pulling force along the axis of the device.

In one aspect of the device, the cylindrical body includes a left handle and a right handle symmetrically opposed to one another with respect to the elongated center portion.

In one aspect of the device, the right and left loop members may symmetrically diverge from the cylindrical body with respect to the central axis.

In one aspect of the device, the left and right loop members may symmetrically rejoin each another with respect to the central axis and proximal to the elongated center portion.

In one aspect of the device, the left and right loop members may be triangular.

In one aspect of the device, the second handle may include a dividing member between the right loop member and left loop member.

In one aspect of the device, the elongated center portion, first handle, and second handle may be integrally formed from the elastic material.

In one aspect of the device, the first handle includes a reinforcement bar.

For a further understanding of the nature and advantages of the invention, reference should be made to the following description taken in conjunction with the accompanying figures. It is to be expressly understood, however, that each of the figures is provided for the purpose of illustration and description only and is not intended as a definition of the limits of the embodiments of the present invention.

BRIEF DESCRIPTION OF THE DRAWINGS

FIG. 1E is a cross-sectional view of the device shown in FIG. 1C.

FIGS. 1N, 1O, and 1P are perspective, top views, and cross-sectional views, respectively, of a device for assisting birth, according to an embodiment of the invention.

DETAILED DESCRIPTION OF THE INVENTION

Embodiments of the invention include a device to provide an effective body position during the second stage of labor. The device utilizes specific muscles to increase effective pushing strength during labor, and thus reducing labor time. The device can also be used for low impact exercises that target the abdominal muscles used in the birthing process.

The device is made of flexible and elastic polymer (e.g., rubber) that stretches during use. The device includes a non-enclosed handle bar for grasping by a pregnant patient. A center portion extends from the handle bar to an enclosed loop, which can be used for anchoring the device to a non-moveable object (e.g., a bed, squatting bar), or for grasping by another person.

In use, a patient would be in a semi to high-fowlers position with her feet placed on a squatting bar or stirrups. The patient grasps the device at the handle bar, with her arms fully extended, and with the device extending between her legs at a downward angle. The loop of the device is either attached to the bed or held by a birthing partner. During a contraction the mother would centrally pull the device towards her causing her to utilize the correct abdominal muscles. By increasing the force exerted by the abdominal muscles during a contraction, interabdominal pressure is increased to help move the fetus down the birth canal, and lengths of the active and pushing stages of labor can be decreased.

Use of the device is especially effective for patients who have epidurals. An epidural can result in the patient having no feeling in the lower half of their body, with little or no sensation of movement or muscle contraction, along with a decreased or non-existent urge to push. Thus, use of the device provides both a physical aide and visual guide for utilizing correct abdominal muscles.

Figure 1A:
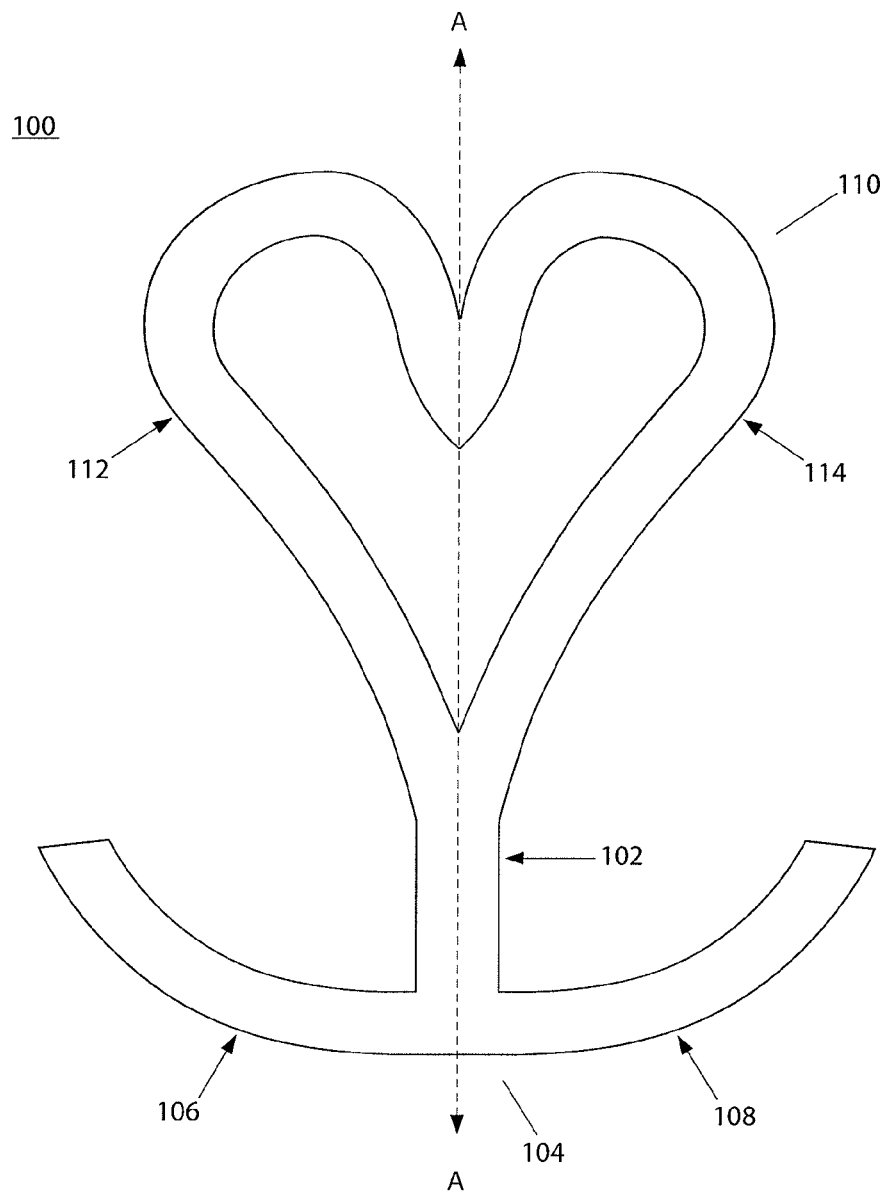
FIGS. 1A-1B and 1C are top views of devices for assisting birth, according to embodiments of the invention.

Exemplary Devices for Assisting Birth:

FIG. 1A shows a device 100 for assisting birth, according to an embodiment of the invention. The device 100 includes an elongated central portion 102 which is positioned along a central axis A-A. The elongated central portion 102 is a cylindrical body with a circular cross-section perpendicular to axis A-A. The cross-sectional area of the cylindrical body can be between about 0.5 in$^2$ and 2 in$^2$ with one embodiment being 1.23 in$^2$ (approx 800 mm$^2$).

A first handle 104 perpendicularly extends as a cylindrical body from a distal portion of the elongated central portion 102. The first handle 104 includes a left handle 106 and a right handle 108, which both eventually curve inwardly in a proximal direction. The left handle 106 and right handle 108 can include padded or soft members, such as foam rubber covering, and/or ergonomic molded finger grips for providing fatigue relief to a patient, as pushing and the second stage of labor can last several hours. The left handle 106 and right handle 108 can have circular cross-sections which can be 32 mm (approximately 1.25 inches) in diameter. The left handle 106 and right handle 108 can have internal reinforcement (e.g., metal or plastic rods) to prevent over-deformation of the left handle 106 and right handle 108 during use. The end to end width of the first handle 104 can be approximately 300 mm (12 inches). The second handle can have sufficient stiffness to inhibit compression of the fingers of an associated hand against each other when the patient applies a birth-assisting pulling force along the axis of the device sufficient to elastically stretch the device.

A second handle 110 extends from a proximal portion of the elongated central portion 102. The second handle 110 is an enclosed handle with at least one loop, which may be open or closed. A right loop member 112 and left loop 114 member extend symmetrically in divergent directions from the elongated central portion 102, and rejoin at a location proximal to the elongated center portion 102 to form a heart shape. The right loop member 112 and left loop member 114 can include padded or soft members, such as foam rubber covering, and/or ergonomic molded finger grips for providing fatigue relief to a birthing partner. In use, the second handle 110 can be held by a birthing partner or hooked around a stationary object. The end to end length of the device 100 can be approximately 325 mm (13 inches). The loop members each have sufficient stiffness to inhibit compression of fingers of an associated hand against each other when the patient applies a birth-assisting pulling force along the axis of the device sufficient to elastically stretch the device. The loop members can also be separated with sufficient stiffness as to inhibit compression of the hands against each other when the patient applies the birth assisting pulling force.

The device 100 can be formed from an elastic and flexible material, such as an elastic polymer material, which could be rubber polyurethane, or foam. Suitable materials include rubber, silicone, or other suitable elastomers. The elastic material can also have slow recoil characteristics, such than when elastically stretched as disclosed herein, the device 100 will slowly recoil instead of quickly recoiling. For example, the device 100 may be able to recoil over a time period of 0.25-2 seconds, which can provide for safer birthing environment. The elongated center portion 102, first handle 104, and second handle 110 can be integrally formed with each other in a casting or molding operation to form the device 100. The elongated center portion 102, first handle 104, and second handle 110 can have circular cross-sections of the same diameter. In one embodiment, the device 100 is formed from a polyurethane or thermoplastic elastomer with a durometer rating ranging from 55-65 Shore A, although other durometer ranges can be suitable as well. One such material is two-part (in uncured form) polyurethane elastomer F-60 A/B manufactured by BJB Manufacturing, Inc.

The device 100 is resistant to stretching, and will only elastically deform when significant force (e.g., 20-150 lbs) is placed upon it, along axis A-A. In use, the device 100 will stretch 25-50 mm (0.5-2 inches), depending on the amount of force used. For example, the device 100 can be configured to stretch 0.5 inch when submitted to 20 lbs of stretching force, and 2 inches when submitted to 80 lbs of stretching force. The device 100 can also be configured to be exclusively used with two people and thus require more stretching force. In many embodiments, the device 100 can be configured to stretch more depending on strength of patient and/or birthing partner, for example in the range of 25-127 mm (1-5 inches). Accordingly, the device 100 can have more than one elongated central portion 102 and/or cross-sectional areas to provide a desired amount of elastic deformation.

Figure 1B:
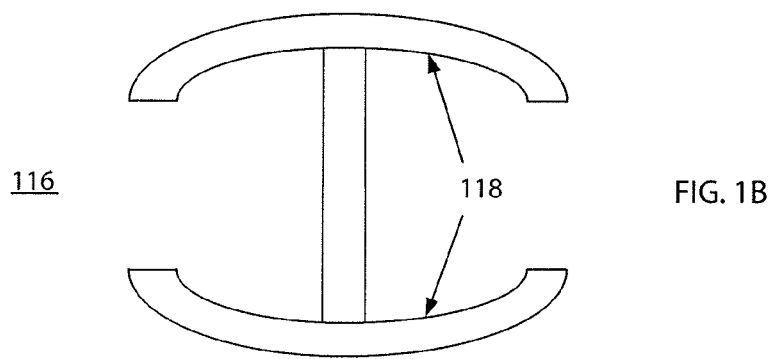
Figure 1C:
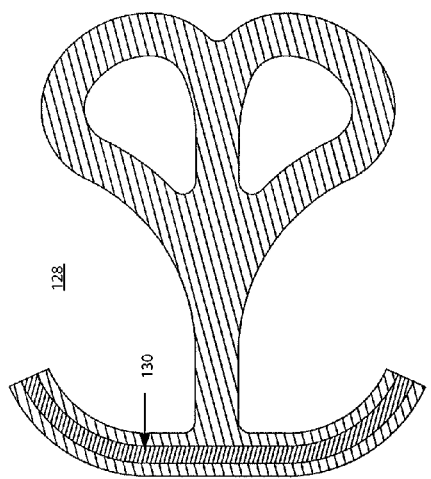
Figure 1D:
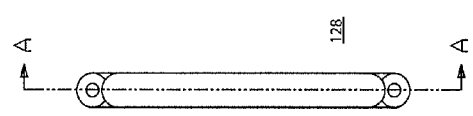
FIG. 1D is a side view of the device shown in FIG. 1C.
Figure 1G:
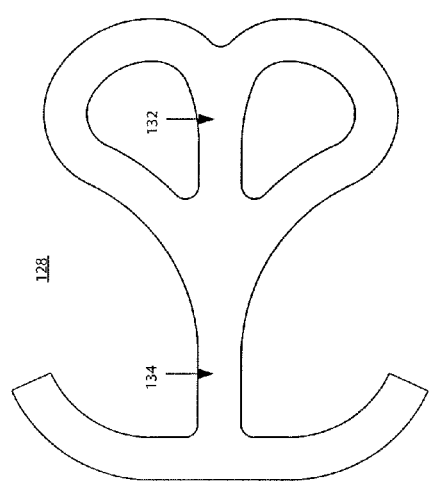
FIGS. 1F and 1G are perspective views of the device shown in FIG. 1C.
Figure 1G:
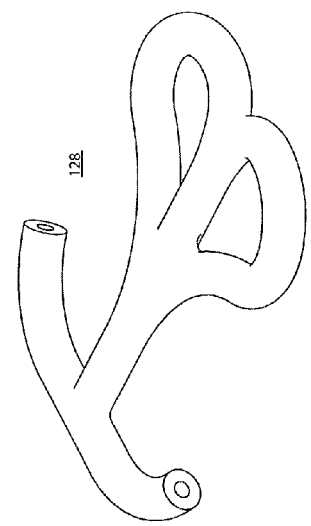
Figure 1F:
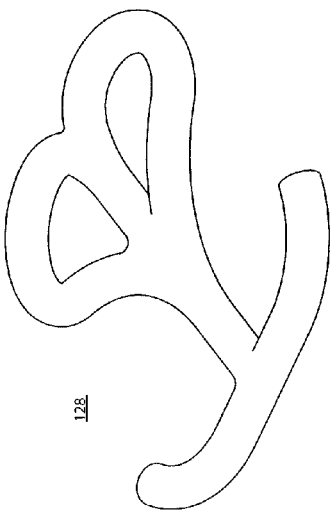

FIG. 1B shows another device 116 for assisting birth, according to an embodiment of the invention. The device 116 shares a similar construction with the previously described device 100, however, device 116 includes two symmetrically located handlebars 118, each of which is similarly configured to the first handle 104. As the handlebars 118 are non-enclosed, the device 116 is primarily intended for use with a birthing partner, although it can be improvised for attachment to a stationary object, for example, by using straps.

FIGS. 1C-1G show yet another device 128 for assisting birth, according to an embodiment of the invention. The device 128 shares a similar construction with the previously described device 100, however, device 128 includes a handle reinforcement bar 130 as shown in cross-sectional view. The handle reinforcement bar 130 supplies handle strength to the device 128, and also can prevent unintended handle deformation during use. The device 128 also includes a handle separator 132, which increases the cross sectional area of the second handle and concentrates elastic stretching of the device 128 to the mid portion 134.

Figure 1H:
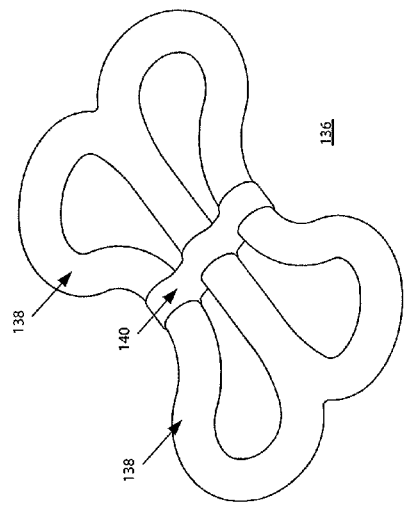
FIGS. 1H and 1I are top and perspective views, respectively, of a device for assisting birth, according to an embodiment of the invention.
Figure 1I:
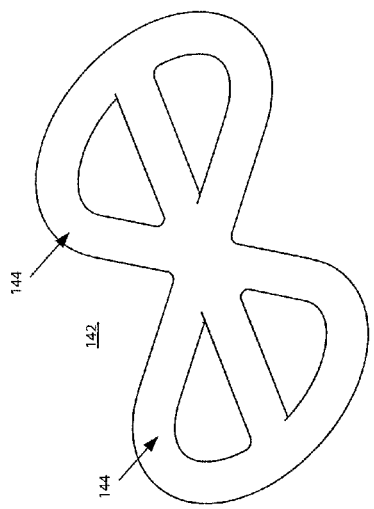

FIGS. 1H and 1I show yet another device 136 for assisting birth, according to an embodiment of the invention. The device 128 shares a similar construction with the previously described device 100. The device 136 includes symmetrical looped handles 138 on both ends. Accordingly, either end of the device 136 can be used by the patient, held by a birthing partner, or attached to a stationary object. The device 136 also includes a central connector 140, which can be an integral molded feature. The central connector 140 has an increased cross-sectional as compared to the handles 138, and thus concentrates elastic stretching of the device 136 to the handles 138.

Figure 1J:
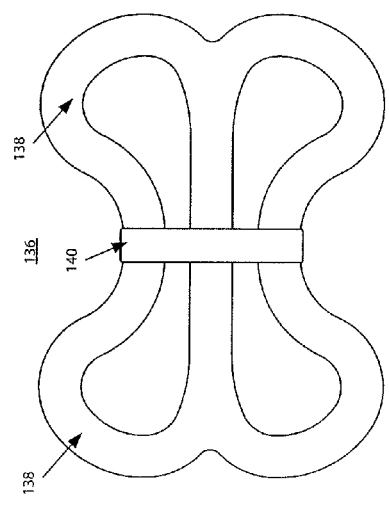
FIGS. 1J and 1K are top and perspective views, respectively, of a device for assisting birth, according to an embodiment of the invention.
Figure 1K:
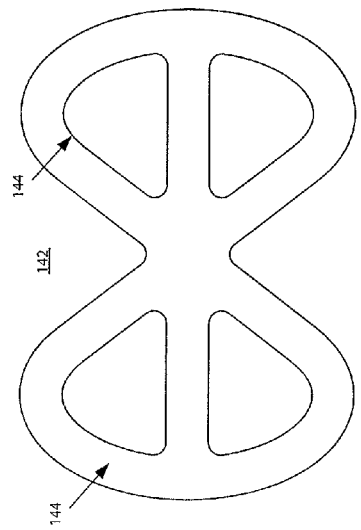

FIGS. 1J and 1K show yet another device 142 for assisting birth, according to an embodiment of the invention. The device 142 shares a similar construction with the previously described device 128. However, the device 142 includes symmetrical looped handles 146 on both ends. Accordingly, either end of the device 142 can be used by the patient, held by a birthing partner, or attached to a stationary object.

Figure 1L:
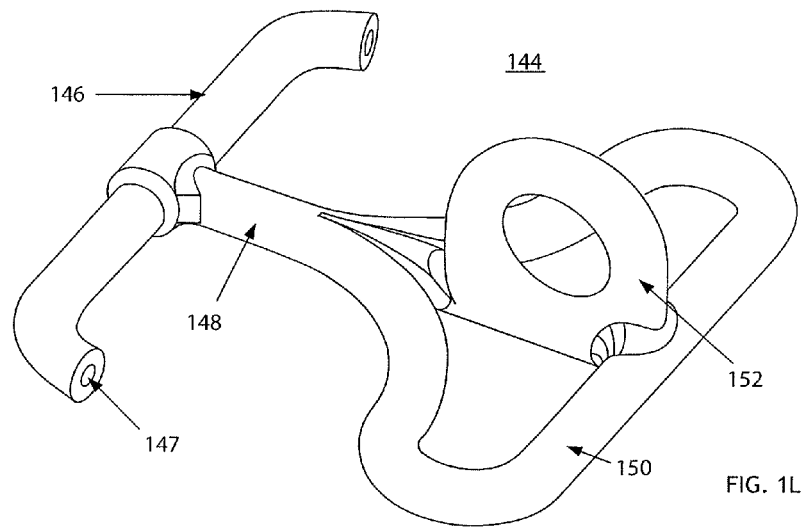
FIGS. 1L and 1M are perspective and top views, respectively, of a device for assisting birth, according to an embodiment of the invention.
Figure 1M:
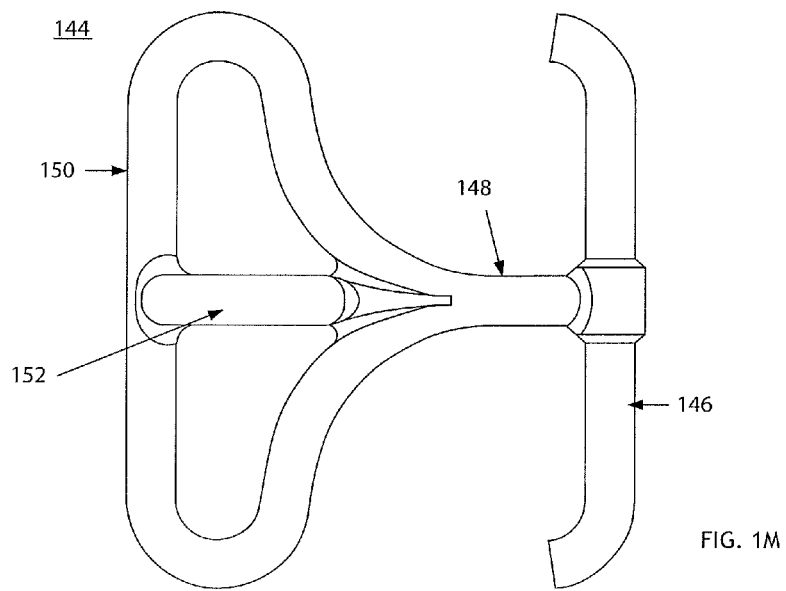

FIGS. 1L and 1M show yet another device 144 for assisting birth, according to an embodiment of the invention. The device 144 shares a similar construction with the previously described device 128. The device includes a handle bar 146, which may include a reinforcement bar 147 as shown in FIG. 1L. The handle bar 146 is integrally formed with an elongated central portion 148. The elongated central portion 148 bifurcates into a looped handle bar 150. The looped handle bar 150 is divided by a central handle 152. The central handle 152 is an encircled loop which transversely extends from the center of the lopped handle bar 150. The central handle 152 can be used for attachment to an immobile object, such as a bed bar.

Figure 1N:
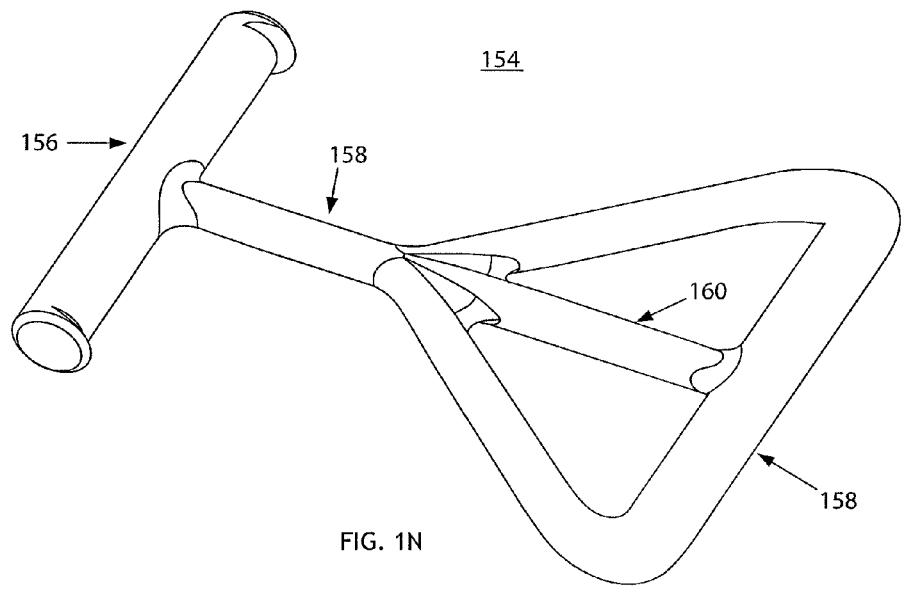
Figure 1O:
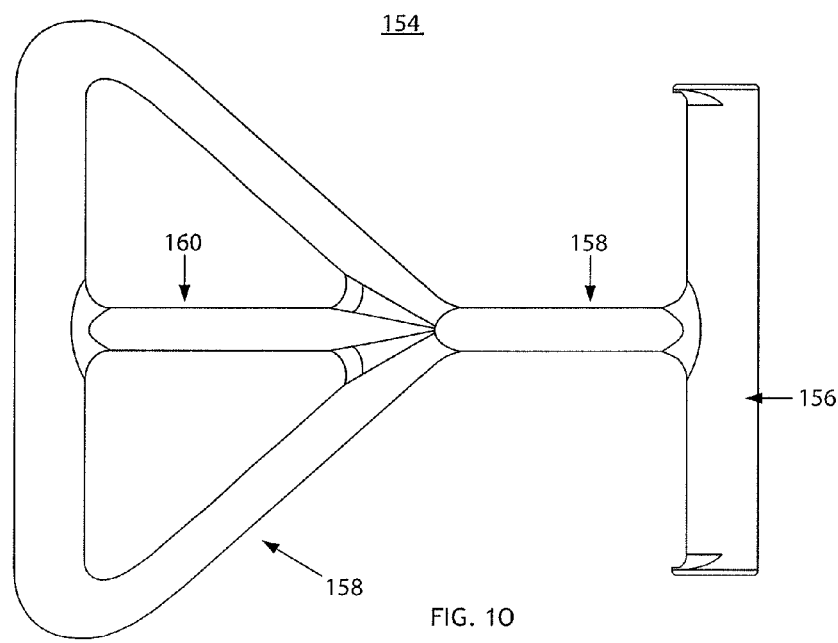

FIGS. 1N, 1O, and 1P show yet another device 154 for assisting birth, according to an embodiment of the invention. The device 154 shares a similar construction with the previously described device 128. The device includes a handle bar 156, which may include an aluminum reinforcement bar or tube molded within, as shown in FIG. 1P. The handle bar 146 is integrally formed with an elongated central portion 148, which in one embodiment is an elongated cylinder that has a diameter of approximately 0.8 in (20.3 mm) and a length of approximately 4 in (102 mm). Due to the having the smallest cross-sectional area along the pulling axis, the elongated central portion 148 generally elastically stretches the most during use, as compared to the rest of the device 154. The elongated central portion 158 is integrally formed with a looped handle bar 158. The looped handle bar 158 has a triangular shape and is centrally and symmetrically divided by a dividing member 160 into left and right loop sections. The dividing member 160 can have webbed transitions into the looped handle bar 158 as shown to reduce stress and propensity for tearing under use. The looped handle bar 158 is generally flexible enough to resiliently fold about the central dividing member 160 in order to allow a straight bed bar to weave through the openings in an over and under fashion.

Figure 2A:
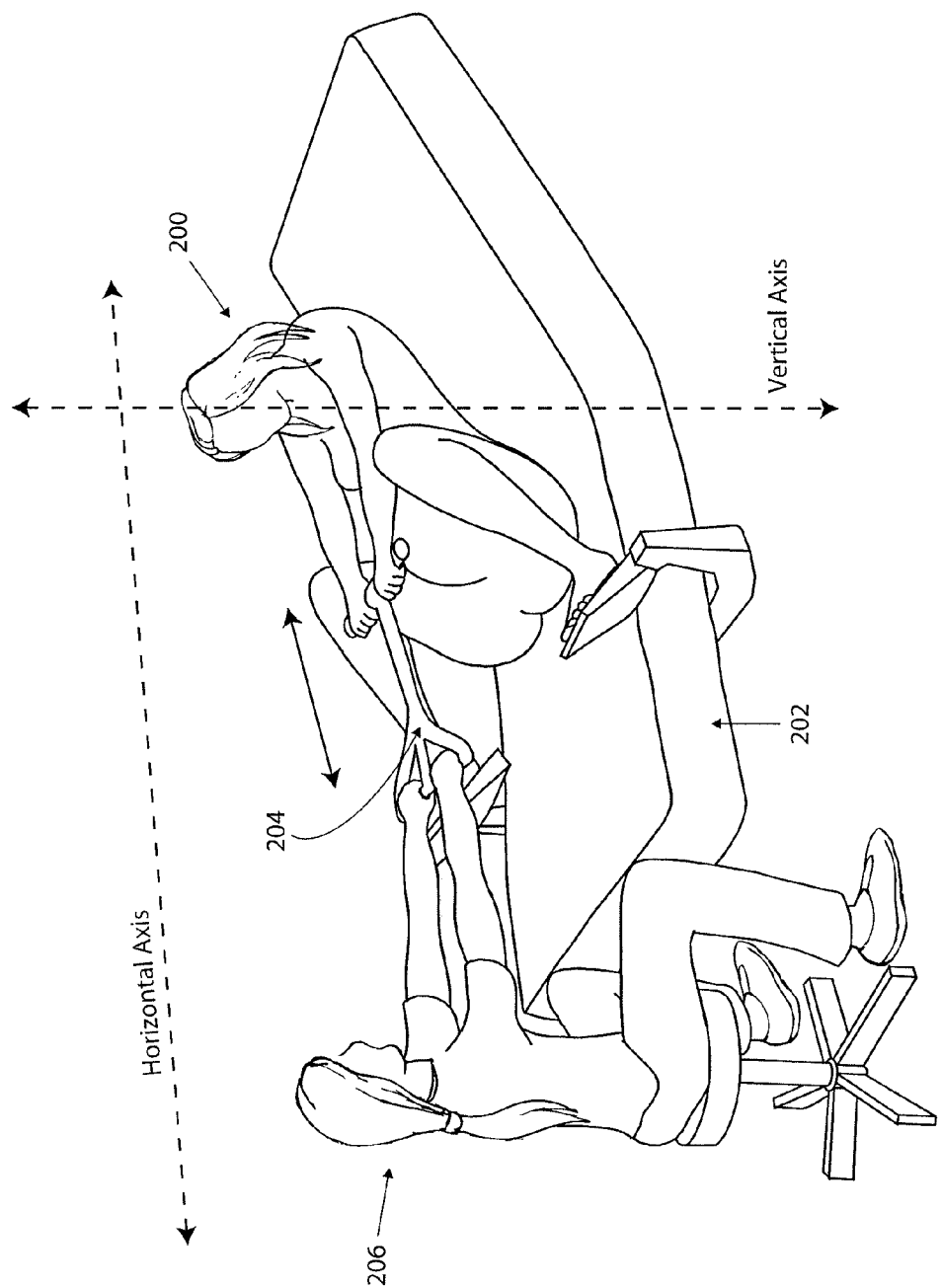
FIGS. 2A and 2B are perspective views of a patient using a device for assisting birth during a contraction, according to embodiments of the invention.
Figure 2B:
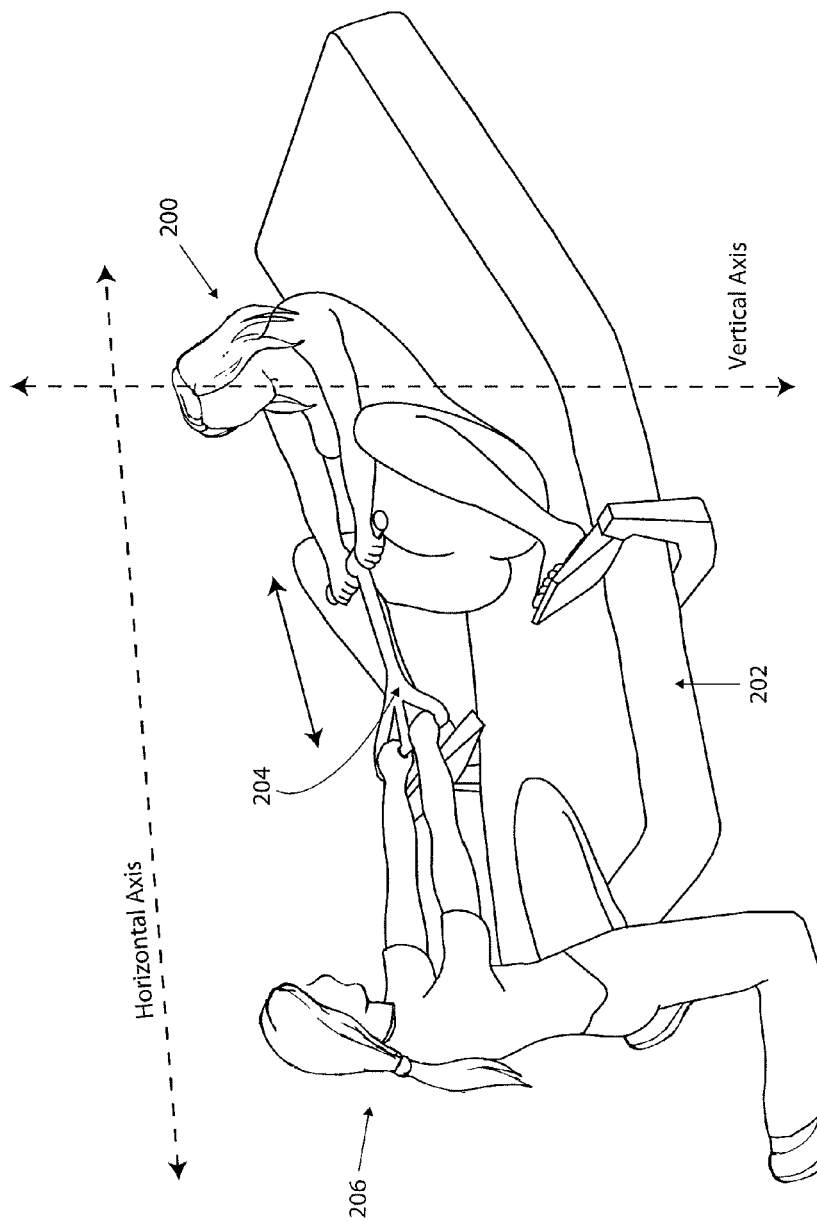

Exemplary Method of Use:

FIGS. 2A and 2B show methods for assisting birth, according to embodiments of the invention.

A pregnant patient 200 is initially positioned on a bed 202 in a semi-fowlers or high fowlers position, while in the second stage of labor. The patient's feet are positioned on a squat bar, stirrups or any other position that allows the patient's legs to be spread and bent in squatting position. A squatting position increases the bearing down sensation experienced by the patient 200, thus, making pushing more effective. An elastic birthing device 204 is placed between the patient's legs, with one end being secured by being attached to a stationary object, or held by a birthing partner 206 as shown. The birthing partner 206 can be in a sitting or standing position while braced against the bed 202. The elastic birthing device 204 can be configured similarly to any of the exemplary birthing devices disclosed herein.

One end of the elastic birthing device 204 is held by the patient, with her arms fully extended and shoulders rounded when pulling. Correct position of the arms forces the patient to utilize stomach muscles, as opposed to arm muscles, when using the elastic birthing device 204. The elastic birthing device 204 is positioned most effectively at a generally downward angle, which can be an angle between the horizontal axis and vertical axis, for example, a 30-45 degree downward angle, with respect to the horizontal axis, may be used.

The elastic birthing device 204 requires large amounts of force to elastically stretch, for example, 20-150 lbs of force. Thus, an average patient can lean slightly backwards and place tension on the elastic birthing device 204 without causing the elastic birthing device 204 to noticeably stretch. Accordingly, by simply holding onto the device as shown, the patient can maintain a correct body position.

As shown, the patient leans back while pulling and stretching the elastic birthing device 204 13-50 mm (0.5-2 inches) during a contraction. The elastic birthing device 204 is stretched by the patient 200 by utilizing her correct abdominal muscles (the rectus abdominus; the external and internal oblique muscles) to pull her body backwards. This motion also causes the muscles of the pelvic floor to assist in the movement of the fetus down the birth canal. By increasing the force exerted by the abdominal muscles during a contraction, interabdominal pressure is increased, and lengths of the active and pushing stages of labor can be decreased. It has been found that use of the elastic birthing device 204 can reduce the time second stage of labor by approximately half, with the potential to reduce cesarean deliveries and vacuum extractions. The downward angle of the elastic birthing device 204 also helps the patient to utilize the correct abdominal muscles, as a higher angle has the tendency to utilize less abdominal muscles and more back muscles.

During the contraction, with the body elevated and the legs off to the sides as far as possible, the patient 200 takes a deep breath and holds it. The patient 200 has her chin placed against her chest and curls around her abdomen while both the birth mother and the other person pulls the device 204 centrally away from each other and down slightly so that the device 204 is over the pelvic region. The force of the pull should be strong enough so that the patient 200 feels the stomach muscles tightening. The patient 200 should be made aware to focus energy in the abdominal area and not somewhere else in her body. For instance, if her upper body or legs are tense, she is likely pushing with those muscles instead of her abdominal muscles.

The patient 200 can try to hold each abdominal push as long as possible while holding her breath. Counting to 10 during the push has been found to be helpful to maintain the force of the push. The patient 200 can then let the breath out completely and quickly take another breath, hold her breath for another 10 count, and then continue this process until the fetus has continued down the birth canal.

The patient's 200 back and shoulders can be rounded forward. This enables the pelvis to open up and for the fetus to come down the birth canal faster. Conversely, arching the back in a reverse direction is not recommended, as this may cause the fetus to go upward in the wrong direction down the birth canal. The birthing partner 206 can provide verbal motivation/instruction to remind the patient to keep the proper body positioning and muscle focus, for example instructing the patient 200 to, "push with your stomach."

A pillow can be placed under that side of the patient's back if it is noticed that the fetus is lying off to one side of the patient's 200 abdomen. The placement of the pillow helps the fetus become more centrally aligned with the birth canal. It should be understood that the positions shown in FIGS. 2A and 2B are not limiting. Accordingly, if one birthing position is ineffective, other positions such as side-lying or sitting up straighter can be used. Care should be taken to make certain that the device 204 is between the patient's 200 legs and over her pelvic region when pushing. It should also be understood that it is generally easier on the birthing partner's 206 back if he/she is sitting opposite the birth mother, or if standing, has one leg (knee) resting on the bed.

The birthing partner 206 may also pull and stretch the device away from the patient 200, and also encourage the patient to use a proper amount of effort during contractions. The birthing partner 206 can assume a sitting position as shown in FIG. 2A or a standing/crouching position as shown in FIG. 2B. The bed 202 may be raised accordingly to place the patient 200 and device 204 at the optimal position for a downward pulling angle. It is important for the birthing partner 206 to brace against the bed 202 with their knees or other body part, to avoid being pulled on top of the patient 200. The birthing partner 206 can pull the elastic birthing device 204 away from the patient in a manner which requires the patient to output a greater force than when the elastic birthing device 204 is attached to a stationary object. Accordingly, in order to assume the position shown and not be pulled forwards, the patient 200 has to overcome the pulling force from the birthing partner 206, as well provide enough force to elastically stretch the elastic birthing device 204. Use of the birthing partner 206 is particularly useful when the patient 200 is especially strong or heavy, or is not putting forth enough effort when using the device 204 alone.

After the contraction, the patient 200 may relax her abdominal muscles which causes the elastic birthing device 204 to elastically reform and place the patient 200 back into a birthing position. The elastic birthing device 204 provides a tensional spring force which helps the patient to maintain positioning. Thus, the elastic birthing device 204 can automatically place the patient when the patient 200 relaxes her muscles to maintain a semi-fowlers or high-fowlers position. Prior art devices do not provide sufficient force to place the patient back into position, and thus can cause a patient to wander from an optimal birthing position after use. Alternatively, the patient 200 may rest against the bed 200 between contractions.

It is important to note that the elastic birthing device 204 also provides a visual confirmation to the patient, that she is utilizing the correct abdominal muscles during a contraction. Many patients have undergone an epidural to eliminate pain, however, a side effect of an epidural is the reduced or complete lack of sensation in the lower body, including muscle feedback. Accordingly, a patient may not be able to discern the difference in contraction efforts, for example, 10 lbs of effort can be physically indiscernible from 50 lbs of effort. As the elastic birthing device 204 requires significant effort to stretch, the patient is provided with a visual indication that she is actually providing the correct amount abdominal effort during a contraction. For example, a patient with an epidural who sees that she is hardly stretching the elastic birthing device 204 during a contraction will know that she needs to increase her effort. This is especially important over a long birthing procedure (e.g., several hours), where fatigue can cause the patient to unconsciously output less force. The elastic birthing device 204 can visibly deform during use, for example by necking of a center portion of the elastic birthing device 204, which provides improved visual confirmation compared to movement alone.

The elastic birthing device 204 can also be used for practicing birth contractions. In one embodiment, the patient 200 can position herself similarly shown in FIG. 2A and utilize her abdominal muscles in preparation for labor by performing sets of simulated contractions, for example, 1-5 sets of 10-50 simulated contractions a day. The elastic birthing device 204 can be hooked around the patient's feet, held by a partner, or attached to a stationary object.

Attachment to a Stationary Object:

FIGS. 3A-3D shows an elastic birthing device 300 being attached to a stationary object, according to an embodiment of the invention. The birthing device 300 is shown in a similar configuration to the birthing device 154 described herein. It should be understood that any of the devices disclosed herein with at least one looped handle may be attached in a similar manner.

Figure 3B:
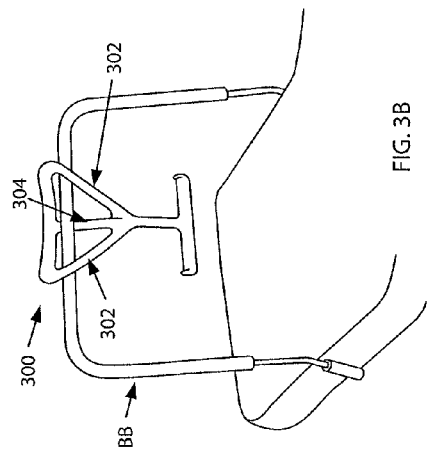
FIGS. 3A, 3B, 3C, and 3D, show views of a device for assisting birth being manipulated for attachment to a birthing bar, according to an embodiment of the invention.
Figure 3D:
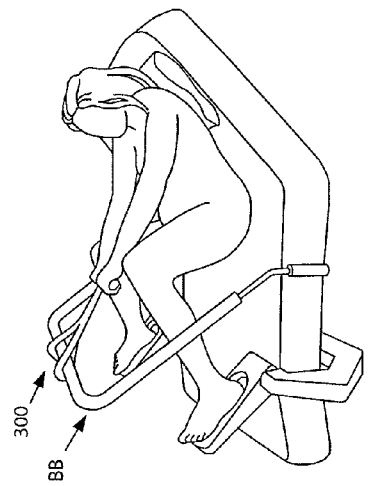
Figure 3A:
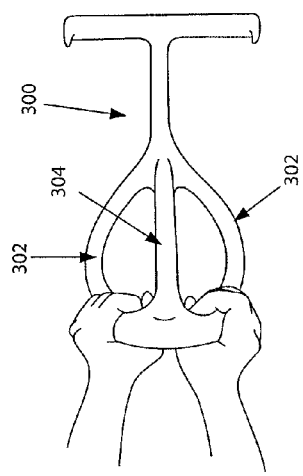

In FIG. 3A the birthing device 300 is manipulated to fold handle sections 302 about dividing member 304. This allows a straight bar to be weaved in and out of the handle sections 302 and the dividing member 304. The flexibility of the material of the birthing device 300 enables the handle sections 302 about dividing member 304 to be manipulated by hand.

In FIG. 3B the birthing device 300 is maintained in the position shown in FIG. 3A and advanced over a birthing bar BB as shown. The two openings of the birthing device looped handle form one opening via the folding operation described above. The birthing bar BB is disconnected from the bed at one end of the birthing bar BB, and the birthing device 300 is advanced over the disconnected end. The birthing bar BB may then be reconnected.

Figure 3C:
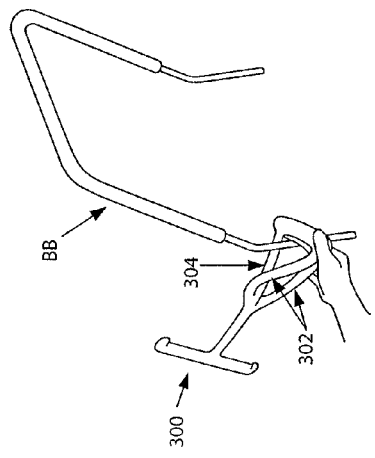

In FIG. 3C the birthing device 300 is positioned over the center portion of the birthing bar BB as shown. The folding operation and subsequent advancement of the birthing device 300 onto the birthing bar BB results in the birthing device 300 woven onto the birthing bar BB. This is shown as the dividing member 304 is located oppositely to handle sections 302 with respect to the birthing bar BB. The resilient nature of the material of the birthing device 300 will maintain the birthing device 300 in position.

In FIG. 3C the birthing device 300 is shown in use on the birthing bar BB by a patient. It should be understood that many hospital supplied birthing bars will not provide the optimum pulling angle for the patient to use, as shown. However, the use of a birthing device 300 at a less than optimum angle is preferable to not using the birthing device 300 at all. In some embodiments, an accessory bar may be attached to the birthing bar BB between the upright members of the birthing bar, and parallel to the center portion of the birthing bar. Accordingly, the birthing device 300 can be attached to the accessory bar to provide an optimum pulling angle for the patient. In all cases, care should be taken to make sure the birthing device 300 is secured to the birthing bar BB or other stationary object to avoid accidental slipping or injury.

As will be understood by those skilled in the art, the present invention may be embodied in other specific forms without departing from the essential characteristics thereof. These other embodiments are intended to be included within the scope of the present invention, which is set forth in the following claims.

What is claimed is:

1. A device for assisting a woman to give birth, the device comprising:
    an elongated center portion with a first end and a second end defining a central axis;
    a first handle connected to the first end, the first handle configured for gripping with two hands; and
    a second handle connected to the second end, the second handle including at least one loop,
    wherein the elongated center portion, first handle, and second handle comprise an elastic material,
    wherein the elongated center portion comprises a single solid elastomer cylinder.

2. The device of claim 1, wherein the elongated center portion has sufficient axial elasticity to increase significantly in length when the woman applies a birth-assisting pulling force along the axis of the device.

3. The device of claim 1, wherein second handle comprises a left handle and a right handle symmetrically opposed to one another with respect to the elongated center portion.

4. The device of claim 3, wherein the right and left handles symmetrically diverge from the cylindrical body with respect to the central axis.

5. The device of claim 4, wherein the left and right handles symmetrically rejoin each another with respect to the central axis and proximal to the elongated center portion.

6. The device of claim 5, wherein the left and right handles are triangular.

7. The device of claim 6, wherein the second handle comprises a dividing member between the right handle and the left handle.

8. The device of claim 1, wherein the elongated center portion, first handle, and second handle are integrally formed from the elastic material as a single body.

9. The device of claim 1, wherein the first handle includes a reinforcement bar.

10. The device of claim 1, wherein the elastomer material comprises a Shore A durometer ranging from 55-65.

11. The device of claim 10, wherein the elongated center portion has a cross-sectional area ranging from 0.5-2.0 in$^2$.

* * * * *